United States Patent
Hartselle

(10) Patent No.: US 9,949,724 B2
(45) Date of Patent: Apr. 24, 2018

(54) SPECIMEN CUP INCLUDING TEST CARD SLOT AND METHOD OF USE THEREOF

(71) Applicant: Larry Hartselle, Huntsville, AL (US)

(72) Inventor: Larry Hartselle, Huntsville, AL (US)

(73) Assignee: Instant Tech Subsidiary Acquisition Inc., Huntsville, AL (US)

( * ) Notice: Subject to any disclaimer, the term of this patent is extended or adjusted under 35 U.S.C. 154(b) by 705 days.

(21) Appl. No.: 13/774,579

(22) Filed: Feb. 22, 2013

(65) Prior Publication Data

US 2014/0242716 A1  Aug. 28, 2014

(51) Int. Cl.
*B01L 3/00* (2006.01)
*A61B 10/00* (2006.01)

(52) U.S. Cl.
CPC .......... *A61B 10/007* (2013.01); *B01L 3/508* (2013.01); *B01L 3/50855* (2013.01)

(58) Field of Classification Search
None
See application file for complete search history.

(56) References Cited

U.S. PATENT DOCUMENTS

| | | |
|---|---|---|
| 4,852,560 A | 8/1989 | Hermann, Jr. et al. |
| 4,865,812 A * | 9/1989 | Kuntz .................... B01L 3/508 356/246 |
| 6,277,646 B1 | 8/2001 | Guirguis et al. |
| 6,379,620 B1 | 4/2002 | Tydings et al. |
| 6,497,843 B2 | 12/2002 | Tydings |
| 6,548,019 B1 | 4/2003 | Lee et al. |
| 6,730,268 B2 | 5/2004 | Lee et al. |
| 6,805,837 B2 | 10/2004 | Tydings |
| 6,805,838 B2 | 10/2004 | Tydings |
| 7,507,373 B2 | 3/2009 | Vallejo et al. |
| 7,560,272 B2 | 7/2009 | Ramsey et al. |
| D610,254 S | 2/2010 | Huff |
| 8,206,661 B2 | 6/2012 | Vallejo et al. |
| 2001/0012637 A1* | 8/2001 | Casterlin ............... A61B 10/007 436/518 |
| 2003/0099572 A1* | 5/2003 | Ng .......................... B01L 3/502 422/417 |
| 2003/0190745 A1* | 10/2003 | Galloway ............ A61B 10/007 435/287.2 |
| 2004/0132091 A1* | 7/2004 | Ramsey ............... A61B 10/007 435/7.1 |
| 2004/0184965 A1* | 9/2004 | Smith ................ A61B 10/0096 422/400 |
| 2010/0278692 A1* | 11/2010 | Chen ....................... B01L 3/508 422/420 |

* cited by examiner

*Primary Examiner* — Scott Long
*Assistant Examiner* — Gary E Hollinden
(74) *Attorney, Agent, or Firm* — DLA Piper LLP (US)

(57) ABSTRACT

A specimen collection cup has a container. The container has a wall and a floor and is configured for receiving and retaining a specimen. A section of the wall is transparent. Further, the container has a tab coupled to an inside surface of the wall that creates a slot for receiving a test card having a reagent pad affixed thereto. The tab is coupled to the inside surface of the wall such that when the test card is inserted in the slot indicia on the test card is aligned with the transparent section.

13 Claims, 5 Drawing Sheets

SPECIMEN CUP INCLUDING TEST CARD SLOT AND METHOD OF USE THEREOF

BACKGROUND

There are a variety of tests that may be used to test whether a donor has partaken in any number of drugs. There are urine tests in which a donor deposits his/her urine into a cup, and test strips that are submerged in the urine. The test strips have drug indication lines that appear or do not appear based on the presence or absence of drugs in the urine.

SUMMARY

A specimen collection cup has a container. The container has a wall and a floor and is configured for receiving and retaining a specimen. A section of the wall is transparent. Further, the container has a tab coupled to an inside surface of the wall that creates a slot for receiving a test card having a reagent pad affixed thereto. The tab is coupled to the inside surface of the wall such that when the test card is inserted in the slot indicia on the test card is aligned with the transparent section.

DRAWINGS

DETAILED DESCRIPTION

Figure 1:
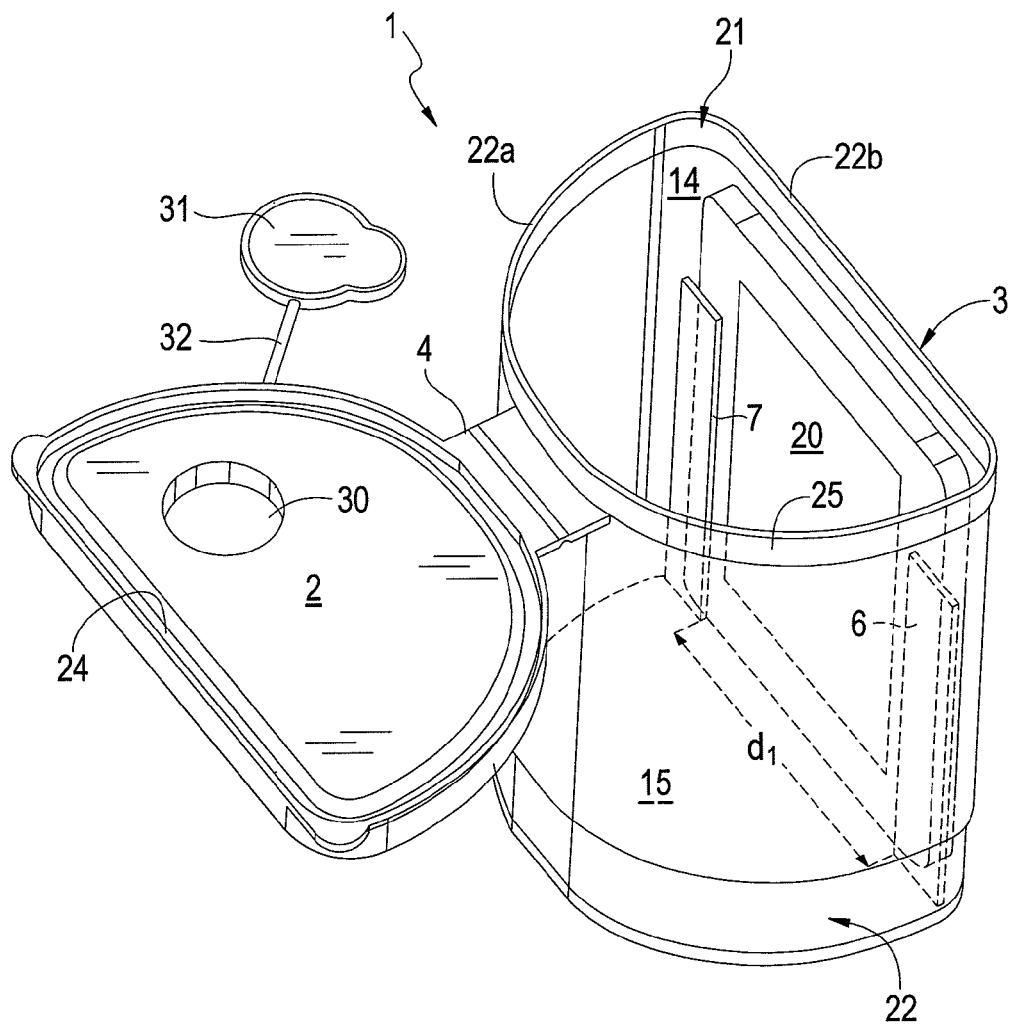
FIG. 1 is a perspective view of a specimen collection cup in accordance with an exemplary embodiment of the present disclosure.

FIG. 1 depicts a perspective view of a specimen collection cup 1 in accordance with an exemplary embodiment of the present disclosure. The specimen collection cup 1 comprises a container 3 and a corresponding lid 2.

The container 3, lid 2, and tab 4 may be made of any type of durable plastic material. In one embodiment, they are made of polyethylene.

In one embodiment, the lid 2 is attached to the container 3 via a tab 4. In such an embodiment, the tab 4 is flexible such that the lid 2 may be rotated relative to the container 3 and coupled to an open end 21 of the container 3.

In the exemplary embodiment depicted in FIG. 1, the container 3 comprises a wall 22. In one embodiment, as shown, the wall 22 comprises an arcuate, e.g., arched, curved, or section 22a that is contiguous with a linear section 22b. Further, the container 3 comprises a floor 15 that is contiguous with the wall 22. The arcuate section 22a and the contiguous linear section 22b forming a semicircle-shaped chamber for collecting a specimen (not shown), e.g., bodily fluid, from a donor.

In one embodiment, the lid 2 is semicircle-shaped and comprises a groove 24. When coupling the lid 2 to the container 3, the groove 24 receives and engages a rim 25. In such an embodiment, the lid 2 snaps onto the container 3 via mating of the groove 24 and the rim 25, and the container 3 contains the specimen once deposited in the container 3.

In one embodiment, the lid 2 comprises an opening 30. The opening 30 may be used to access the specimen once the lid 2 has been attached to the container 3. Such access may allow all or a portion of the specimen to be removed without removing the lid 2. In addition, the opening 30 may allow objects, e.g., test strips, to be inserted into the container 3 so that it may contact specimen contained in the container 3. Further, the lid 2 is attached to a top 31 that may be coupled to the opening 30 to further retain the specimen within the container 3 when the lid 2 is coupled to the container 3. Note that in the embodiment shown in FIG. 1 the top 31 is coupled to the lid 2 via a tether 32; however, the top 31 need not be attached to the lid 2 or other types of attachment mechanisms may be used in other embodiments. Note that the openings 30 and 31 may be present in exemplary embodiments. However, such openings 30 and 31 may also be removed in other embodiments.

The container 3 further comprises two tabs 6 and 7 that are coupled to an inside surface of the wall 22. As will be shown with reference to FIG. 2, the tabs 6 and 7 are coupled to the wall 22 such that slots are formed for receiving a test strip card 20, which is described further herein. To minimize cost and interference with the specimen and to allow a portion of the specimen to contact necessary portions of the test strip card 20, the tabs 6 and 7 are spaced apart a distance $d_1$. Thus, specimen retained in the container 3 may react with the necessary portions of the test card 20 and provide test results identifying the presence/absence of chemicals in the specimen.

Figure 2:
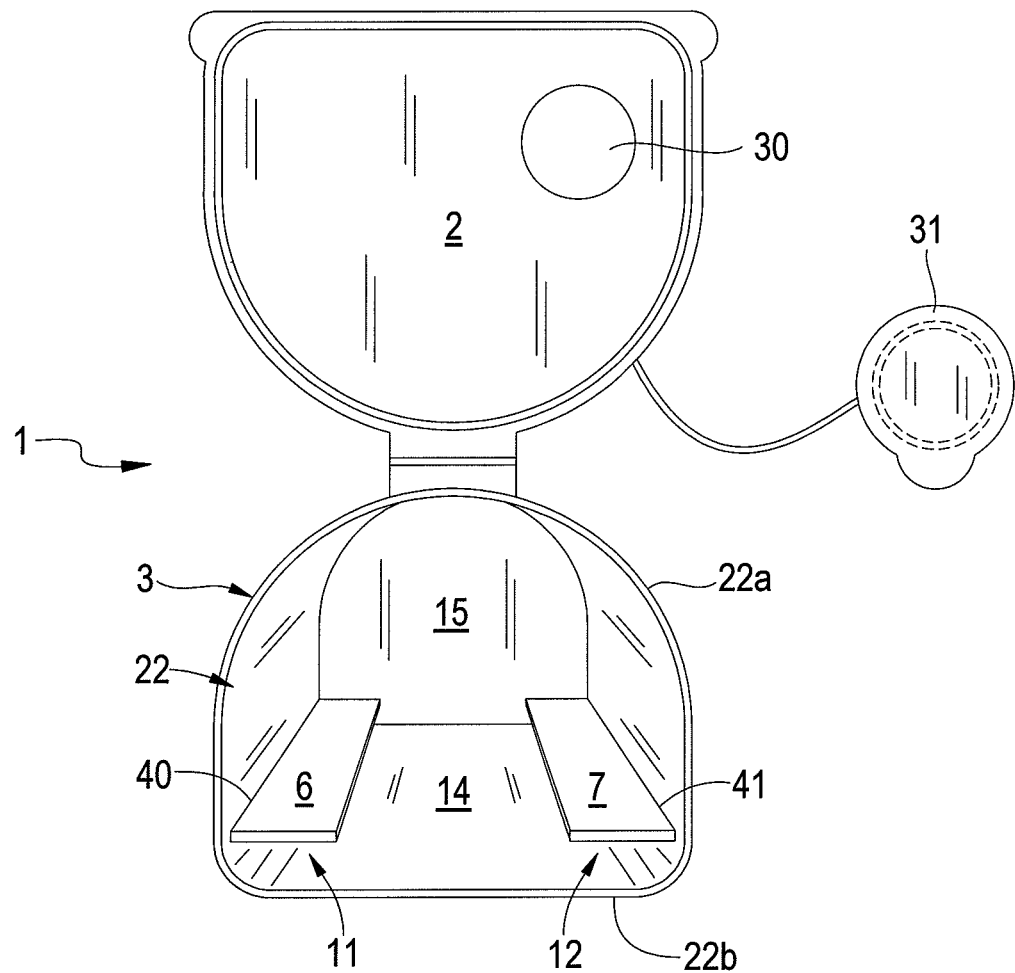
FIG. 2 is a top view of the specimen cup such as is shown in FIG. 1.

FIG. 2 depicts a top view of the specimen collection cup 1 when the lid 2 is not coupled to the container 3, i.e., the specimen collection cup 1 is in an open position.

In the embodiment depicted in FIG. 2, edges 40 and 41 of the tabs 6 and 7, respectively, are coupled to an inside surface 60 of the arcuate section 22a of the wall 22. The tabs 6 and 7 are coupled to the inside surface 60 of the arcuate section 22a of the wall 22 at distances $d_2$ and $d_3$, respectively, from an inside surface 15 of the linear section 22b of the wall 22. Thus, slot 11 is formed between the tab 6 and the inside surface 14 of the linear section 22b, and slot 12 is formed between the tab 7 and the inside surface 14 of the linear section 22b.

Figure 3:
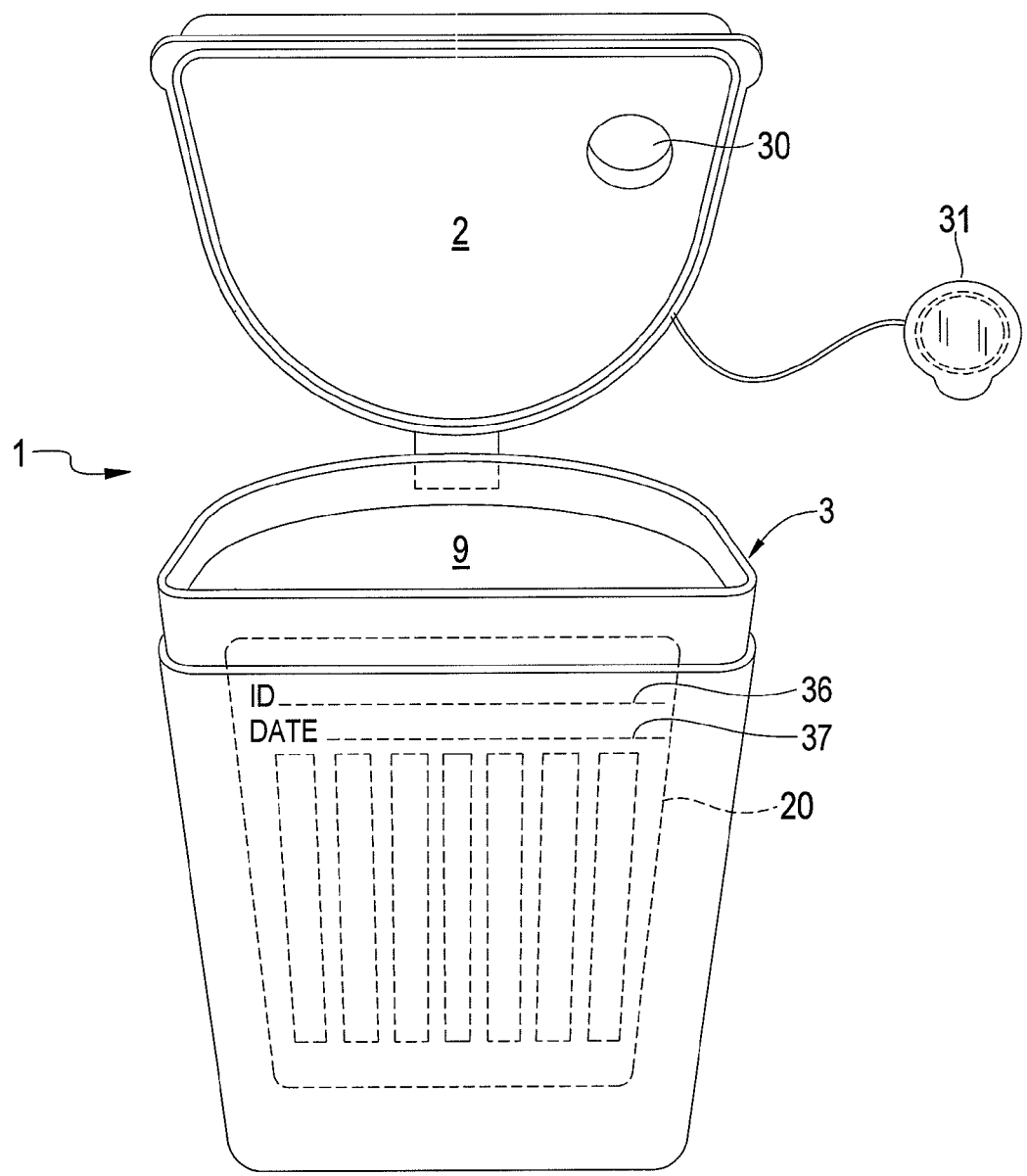
FIG. 3 is a front view of the specimen cup such as is shown in FIG. 1 depicted with an open top.

FIG. 3 depicts a front view of the specimen collection cup 1 when a card 20 is inserted into the slots 11 and 12 and retained within the container 3. Note that in one embodiment, the linear section 22b (FIG. 2) of the wall 22 is transparent and flat. Thus, when the card 20 is inserted within the slots 11 and 12, indicia printed on the card 20 that is adjacent the linear section 22b is readily visible through the flat, transparent wall 22. Thus, when a user of the specimen collection cup 1 desires to view results of a test of a specimen contained in the container 3, the user does not have to open the lid 2. Instead, the user need only look at the linear section 22b of the wall to see results of a drug screening.

Figure 4:
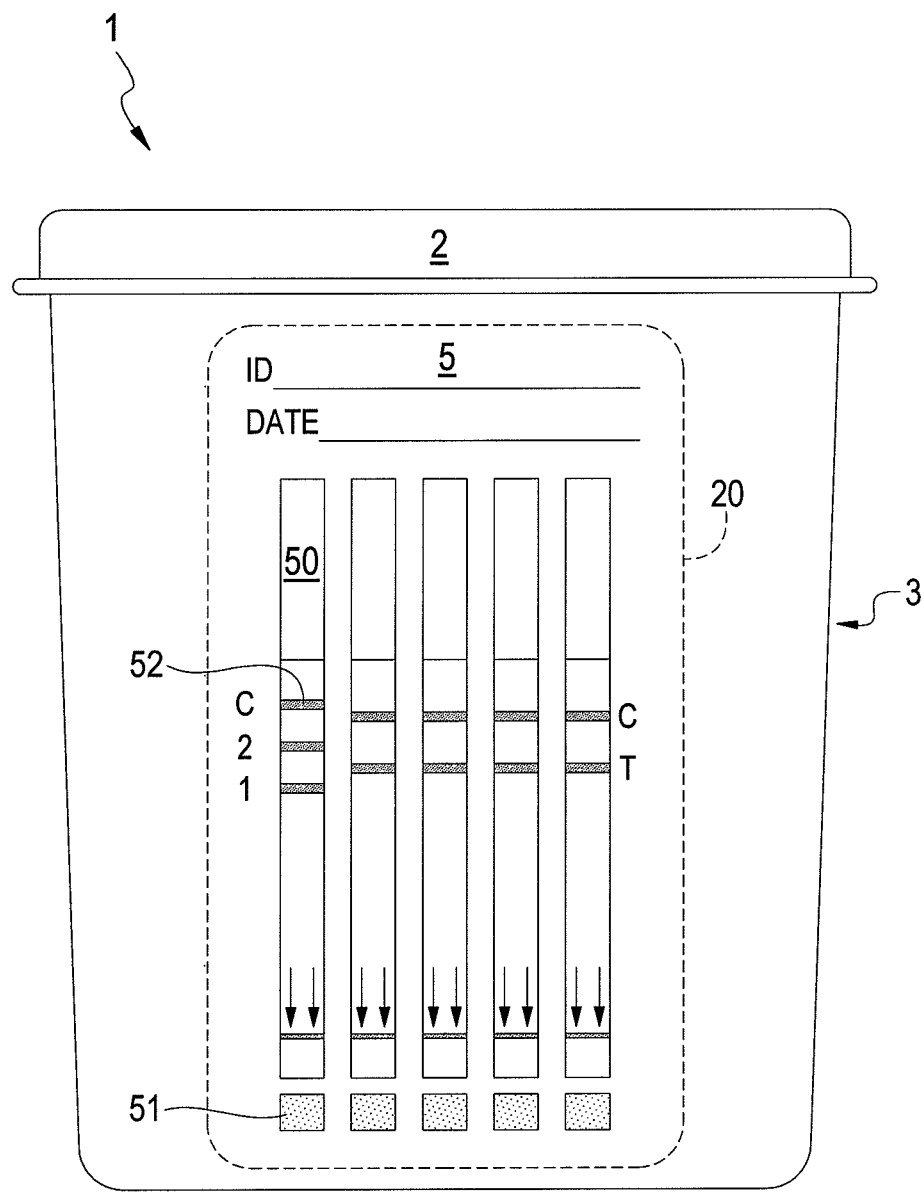
FIG. 4 is a front view of the specimen cup as is shown in FIG. 1 depicted with a closed top and a detailed view of a test strip card exposed from a transparent wall of the specimen cup.

FIG. 4 depicts a front view of the specimen collection cup 1. The test strip card 20 has been inserted into the slots 11 and 12 (FIG. 2) and retained within the container 3. As noted hereinabove, in one embodiment, the linear section 22b of the wall 22 is transparent. Thus, once a specimen is deposited within the container 3, the user may view results of a drug screening through the transparent linear wall 22b.

Note that the test strip card 20 may comprise an area 36 and 37 for noting an identifier and/or a date, respectively, associated with the donor who is depositing the specimen. In addition, the test strip card 20 comprises one or more test strips 50 that comprise chemical pads or reagent pads 51 that react with chemicals present in the specimen contained within the container 3. In this regard, each strip 50 is associated with a particular chemical that may be found in the specimen within the container 3.

In operation, as the donor's specimen saturates the reagent pad 51, the specimen is absorbed by the test strips 50. As the specimen is absorbed by the strip 50, the strip 50 may change colors, e.g., pink. If the drug(s) is detected, a line 52 will not appear for the drug that is being tested. If a drug(s) is not detected, a line will appear for the drug(s) that is being tested. There may also be control lines at an end of the strip 50 that appear to indicate that the test ran properly.

Figure 5:
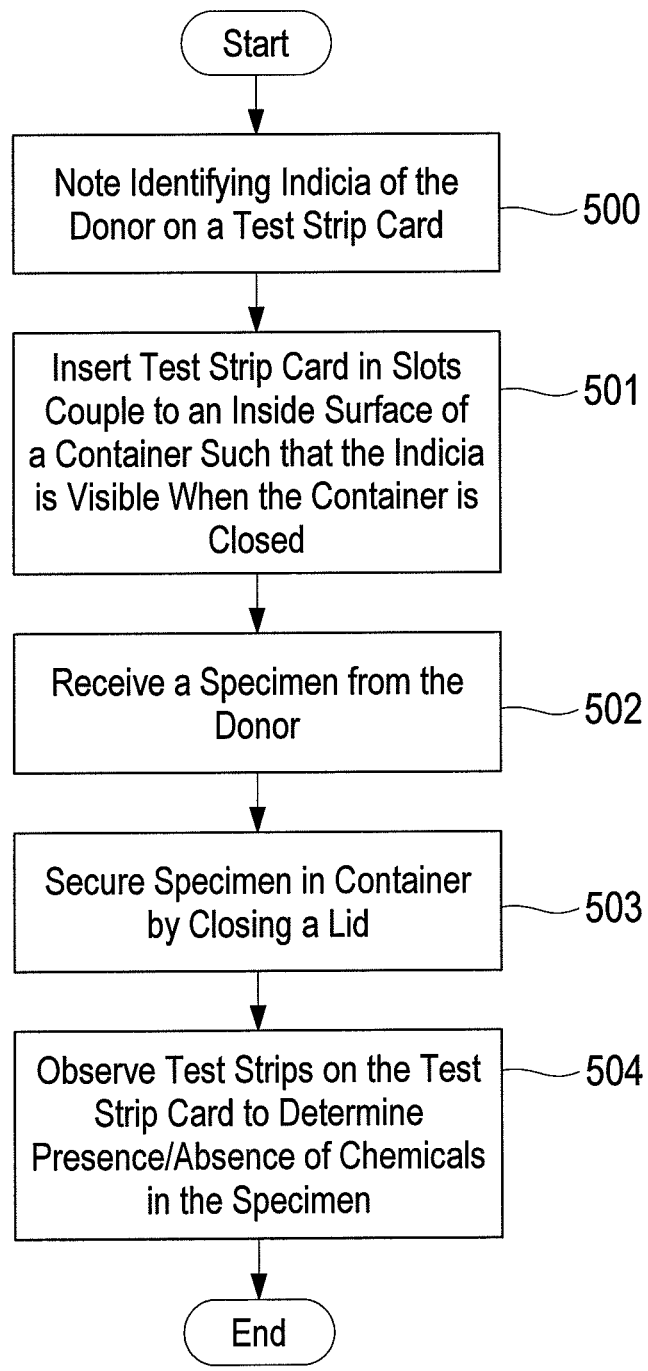
FIG. 5 is a flowchart of an exemplary method in accordance with an embodiment of the present disclosure.

FIG. 5 depicts a flowchart for an exemplary method in accordance with an embodiment of the present disclosure. In step 500, a user, e.g., a test facilitator notes identifying indicia of the donor on a test strip card 20 (FIG. 4). Such identifying indicia may include an identification number or a donor's name. In addition, the test facilitator may note a date on the test strip card 30.

In step 501, the test facilitator inserts the test strip card 20 within slots 11 and 12 (FIG. 2) that are coupled to an inside surface 60 (FIG. 2) of an arcuate section 22*a* (FIG. 2) of a wall 22 (FIG. 2) of a container 3 (FIG. 2). Such test strip card 20 is inserted within the slots 11 and 12 such that the indicia and test strip 50 are visible through the transparent linear section 22*b* (FIG. 2) of the wall 22.

In step 502, a donor deposits a specimen, e.g., urine, within the container 3. Thus, the retainer 3 receives the specimen such that the specimen contacts reagent pad 51 on the test strip card 20. In one embodiment, the donor may deposit a specimen prior to the card being inserted. In such an embodiment, once the donor has made the deposit of the specimen, the facilitator may take possession of the specimen collection cup 1 (FIG. 1) and inserts the test strip card 20.

In step 503, the test facilitator or the donor closes the lid 2 (FIG. 2) thereby retaining the specimen within the container 3. In step 504, the test facilitator (or the donor) observes the test strip 50 on the test card 20 to determine the presence/absence of particular chemicals within the deposited specimen.

The invention claimed is:

1. A specimen collection cup, comprising:
   a container having a longitudinal axis, the container comprising a floor disposed perpendicular to the longitudinal axis and a wall contiguous with the floor and extending along the longitudinal axis thereby defining a chamber configured for receiving and retaining a specimen, the wall comprising a transparent section and a rim defining an opening opposing the floor, wherein the wall of the container comprises a linear portion defining a flat planar surface extending along the longitudinal axis terminating at the rim, and wherein the wall of the container comprises an arcuate portion defining a curved planar surface extending along the longitudinal axis terminating at the rim, the rim having a geometry which conforms to the arcuate portion of the wall and the linear portion of the wall; and
   a first tab coupled to an inside surface of the wall and creating a slot for receiving a test card having a reagent pad affixed thereto, the tab coupled to the inside surface such that when the test card is inserted in the slot, indicia on the test card is aligned with the transparent section.

2. The specimen collection cup of claim 1, wherein the arcuate portion is a semi-circle.

3. The specimen collection cup of claim 1, wherein the flat planar surface is transparent thereby allowing indicia on the test card to be visible to a facilitator when the test card is inserted within the slot.

4. The specimen collection cup of claim 1, further comprising a second tab coupled to the inside surface.

5. The specimen collection cup of claim 4, wherein a first edge of the test card is inserted in the slot formed by the first tab and the inside surface of the wall and a second edge of the test card is inserted in a slot formed by the second tab and the inside surface of the wall such that the test card is adjacent the planar surface when inserted within the container.

6. The specimen collection cup of claim 5, wherein when the test card is inserted into the first and second slots a portion of the test card is exposable to a specimen contained in the container.

7. A specimen collection method, comprising:
   inserting a test card in a container,
   wherein the container has a longitudinal axis and comprises:
   a) a floor disposed perpendicular to the longitudinal axis and a wall contiguous with the floor and extending along the longitudinal axis thereby defining a chamber configured for receiving and retaining a specimen, the wall comprising a transparent section and a rim defining an opening opposing the floor, wherein the wall of the container comprises a linear portion defining a flat planar surface extending along the longitudinal axis terminating at the rim, wherein the wall comprises an arcuate portion defining a curved planar surface extending along the longitudinal axis terminating at the rim, the rim having a geometry which conforms to the arcuate portion of the wall and the linear portion of the wall; and
   b) a first tab coupled to an inside surface of the wall and creating a slot for receiving the test card having a reagent pad affixed thereto, the first tab coupled to the inside surface such that when the test card is inserted in the slot, indicia on the test card is aligned with the transparent section;
   receiving a specimen from a donor deposited within the container;
   viewing indicia on the test card through the transparent section of the wall; and
   determining the presence/absence of chemicals within the specimen based upon the viewing step.

8. The specimen collection method of claim 7, wherein the arcuate portion is a semi-circle.

9. The specimen collection method of claim 7, wherein the planar surface is transparent thereby allowing indicia on the test card to be visible to a facilitator when the test card is inserted within the slot.

10. The specimen collection method of claim 7, wherein the inserting step further comprises inserting the test card within the slot wherein the slot is created via the first tab and a second tab coupled to the inside surface.

11. The specimen collection method of claim 10, wherein the inserting step further comprises inserting the test card within the slot wherein the first and second tabs are adjacent the flat planar surface.

12. The specimen collection method of claim 11, wherein the inserting step further comprises inserting the test card into the slot wherein a first edge of the test card is inserted into the slot formed by the first tab and the inside surface of the wall and a second edge of the test card is inserted in a slot formed by the second tab and the inside surface of the wall such that the test card is adjacent the planar surface when inserted within the container.

13. The specimen collection cup of claim 12, wherein a portion of the test card is exposable to a specimen contained in the container when inserted.

* * * * *